(12) United States Patent
Schmitt-Manderbach et al.

(10) Patent No.: US 9,161,687 B2
(45) Date of Patent: Oct. 20, 2015

(54) DEVICE FOR INTERFEROMETRICALLY MEASURING THE EYE LENGTH AND THE ANTERIOR EYE SEGMENT

(75) Inventors: Tobias Schmitt-Manderbach, Jena (DE); Daniel Bublitz, Rausdorf (DE); Roland Bergner, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 155 days.

(21) Appl. No.: 13/995,351

(22) PCT Filed: Dec. 17, 2011

(86) PCT No.: PCT/EP2011/006395
§ 371 (c)(1),
(2), (4) Date: Sep. 3, 2013

(87) PCT Pub. No.: WO2012/084170
PCT Pub. Date: Jun. 28, 2012

(65) Prior Publication Data
US 2013/0335706 A1    Dec. 19, 2013

(30) Foreign Application Priority Data
Dec. 20, 2010  (DE) .......................... 10 2010 055 350

(51) Int. Cl.
*A61B 3/10* (2006.01)
*A61B 3/117* (2006.01)
*G01B 9/02* (2006.01)

(52) U.S. Cl.
CPC .............. *A61B 3/1005* (2013.01); *A61B 3/102* (2013.01); *A61B 3/117* (2013.01); *G01B 9/02028* (2013.01)

(58) Field of Classification Search
CPC .............................. A61B 3/1005; A61B 3/102
See application file for complete search history.

(56) References Cited

U.S. PATENT DOCUMENTS

| | | | |
|---|---|---|---|
| 7,380,939 B2 | 6/2008 | Barth et al. | |
| 2005/0203422 A1* | 9/2005 | Wei | ................ 600/476 |
| 2007/0258095 A1 | 11/2007 | Olivier et al. | |
| 2008/0285043 A1* | 11/2008 | Fercher et al. | ................ 356/451 |
| 2010/0271594 A1* | 10/2010 | Bergner et al. | ................ 351/206 |
| 2010/0284021 A1 | 11/2010 | Hacker | |
| 2011/0255054 A1 | 10/2011 | Hacker et al. | |
| 2012/0013913 A1* | 1/2012 | Ignatovich et al. | ........... 356/479 |

FOREIGN PATENT DOCUMENTS

| | | |
|---|---|---|
| DE | 198 57 001 A1 | 6/2000 |
| DE | 10 2007 046 507 A1 | 4/2009 |
| DE | 10 2008 051 272 A1 | 4/2010 |

(Continued)

*Primary Examiner* — Jordan Schwartz
(74) *Attorney, Agent, or Firm* — Patterson Thuente Pedersen, P.A.

(57) ABSTRACT

The invention relates to a solution for interferometrically measuring the eye length and the anterior eye segment after the optical axis of the measuring system has been aligned with the optical axis of an eye. The device according to the invention for interferometrically measuring the eye length and the anterior eye segment consists of an illumination source, at least one interferometric measuring array with external reference, diverse optical imaging systems, and a control and evaluation unit. The illumination source has high spatial coherence and low coherence of time. Preferably, light is emitted by the illumination device from the NIR range, having a wavelength of 700-1000 nm, for example. Furthermore, an optical imaging system is arranged in front of the eye such that the illumination light impinges on the eye as a nearly collimated beam.

17 Claims, 4 Drawing Sheets

(56) References Cited

FOREIGN PATENT DOCUMENTS

| | | |
|---|---|---|
| DE | 10 2008 063 225 A1 | 7/2010 |
| DE | 10 2009 022 958 A1 | 12/2010 |
| WO | WO 03/086180 A2 | 10/2003 |
| WO | WO 2007/053971 A1 | 5/2007 |
| WO | WO 2007/065670 A2 | 6/2007 |
| WO | WO 2009/061756 A1 | 5/2009 |

\* cited by examiner

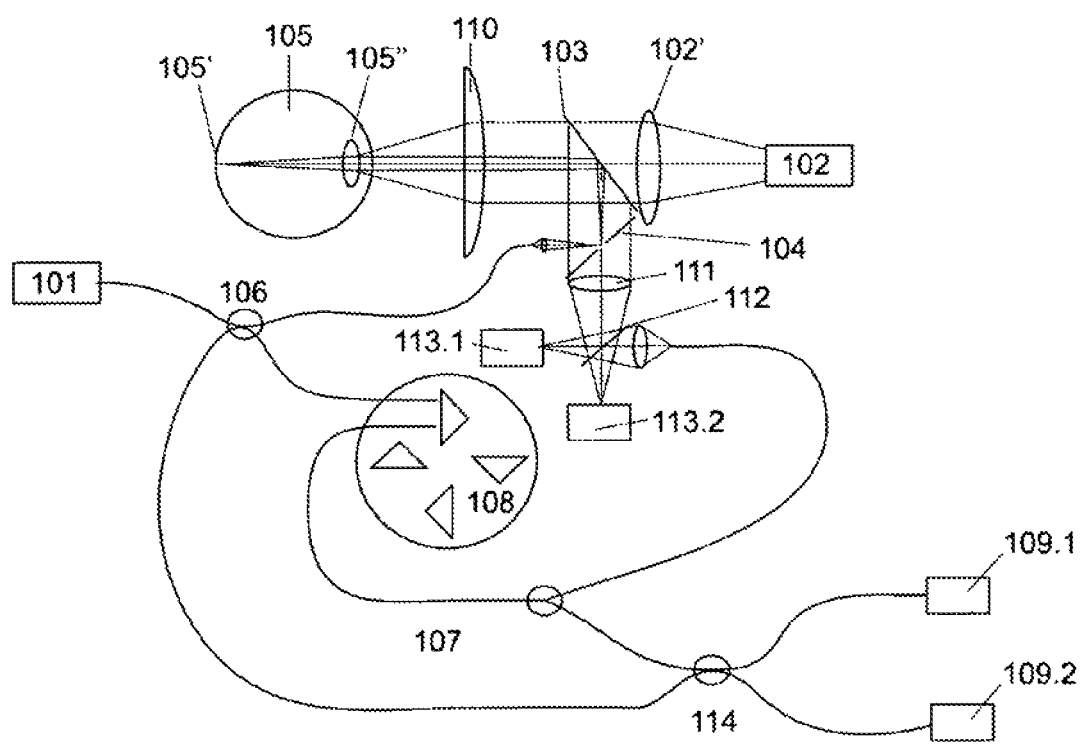
Figure 3b

DEVICE FOR INTERFEROMETRICALLY MEASURING THE EYE LENGTH AND THE ANTERIOR EYE SEGMENT

RELATED APPLICATIONS

The present application is a National Phase entry of PCT Application No. PCT/EP2011/006395, filed Dec. 17, 2011, which claims priority from DE Application No. 10 2010 055 350.6, filed Dec. 20, 2010, which applications are hereby incorporated by reference herein in their entirety.

FIELD OF THE INVENTION

The present invention relates to an approach for interferometrically measuring the eye length and the anterior portion of the eye after the optical axis of the measuring system has been aligned with the optical axis of an eye.

BACKGROUND

The optical axis of the eye is characterized by the straight line between the centers of curvature of refractive surfaces, while the visual axis refers to the axis extending from the "fovea centralis," through the nodal point of the eye, to the fixation object. If the various media are reduced by computation to a single medium having average refractive power and spherical curvature, a point in the eye may be indicated through which all beams pass uninterrupted. This point is referred to as the nodal point of the visual axes.

In all eyes, the visual axis generally deviates from the optical axis. This results, on the one hand, from aberrations of the eye, for example due to the fact that radii of curvature of the individual ocular media are not uniform, the lens of the eye is tilted, the retina is not situated in the focus of the lens of the eye, and many other factors. On the other hand, when the eye is aligned with an object, an attempt is made to image this object to the greatest extent possible in the fovea, which is the area of sharpest vision.

Although the alignment of the eye plays no role in many examinations in ophthalmology, at least the knowledge of its orientation with respect to the opthalmological device is absolutely necessary, not only for treatment, but also for measurement, of the eye.

The measurement of various parameters of an eye is necessary in particular prior to a surgical procedure for substituting an artificial lens of the eye (intraocular lens (IOL)) when clouding of the natural lens (cataract) is present. To ensure optimal vision after the procedure, these parameters must be determined with sufficiently high accuracy to subsequently allow a suitable replacement lens to be selected based on the determined measured values. The most important parameters to be determined include, among others, the axis length (distance from the cornea to the retina), the corneal curvature and refractive power, and the length of the anterior chamber (distance from the cornea to the lens of the eye).

Thus, for carrying out measurements on the eye it is advantageous for the optical axis of the opthalmological measuring system and the optical axis of the eye to be measured to be aligned with one another. In measurements according to the principle of short coherence interferometry, it may thus be ensured that the weak light components reflected from the boundary surfaces of the cornea and the lens reach the detector with adequate signal intensity and produce a measurable interference contrast.

The major technological advantage of OCT is the decoupling of the depth resolution from the transverse resolution. The depth resolution is determined only by the utilized bandwidth of the light source used. Common bandwidths are in the range of several nanometers to over one hundred nanometers, and when measuring radiation in the near infrared is used, 700-1350 nm. The depth resolutions thus achievable are in the range of 3-100 μm. In contrast to microscopy, the three-dimensional structure of the object to be examined may thus be detected, even when the numerical aperture, for example for small pupils in nondilated eyes, is greatly limited.

The purely reflective, and therefore contactless, measurement allows the generation of microscopic images of living tissue (in vivo). The wavelength of the measuring radiation to be used is determined by the desired application, taking into account the wavelength-dependent tissue absorption and back-scattering. If the ocular fundus, for example, is to be measured, in particular radiation in the range of 690-900 nm or 960-1100 nm is suitable, and for the anterior portion of the eye, for example radiation in the range of 1260-1360 nm is suitable.

Various approaches are known according to the prior art for interferometrically measuring the eye length and/or the anterior portion of the eye.

Thus, U.S. Pat. No. 7,380,939 B2 describes an approach for interferometric measurement of the anterior portion of the eye according to the so-called "dual beam" principle. This method requires careful adjustment of the measuring device and a targeted setting of the viewing direction of the patient. For this purpose, the eye is illuminated by a convergent beam bundle and aligned with the optical axis of the measuring system by generating directional stimuli and accommodation stimuli by use of a display which is reflected into the beam path. In clinical practice, adjusting these conditions is time-consuming, and with uncooperative patients is sometimes not possible at all.

An alternative approach is described in WO 2007/053971 A1, in which, instead of the reflected light resulting on the boundary surfaces in the eye, uses volume-scattered light which is back-scattered in a fairly large angular range. The volume-scattered light is usually detected in a diffraction-limited manner. This may preferably be carried out using optical single-mode fibers. However, the usable signal intensity is dependent on the scattering properties of the ocular media, and is generally much smaller than the directly reflected signal components. Patients who have already received an artificial lens cannot be measured in this manner.

A device is known from DE 198 57 001 A1 which may be used for contactless measurement of the eye length, corneal curvature, and depth of the anterior chamber. The axis length is determined interferometrically, the corneal curvature is determined by image processing based on reflected images from measuring marks projected onto the cornea at a certain angle, and the depth of the anterior chamber is determined from the evaluation of the back-scattering of slitted illumination of the lens of the eye. The described measurement of the depth of the anterior chamber does not function for pseudophakic eyes, since the implanted intraocular lenses (IOL) generally have no scattering effect.

For the measurement, the eye must be aligned in such a way that its optical axis coincides with the measuring axis of the device. To this end, collimated fixation light is directed onto the patient along a fixed (coaxial) axis, and is coupled via a mirror for the eye to be measured. An angle between the visual axis of the patient and the measuring axis of the test assembly is set using a scanning mirror.

Interferometric methods for measuring the eye length according to the "dual beam" principle are characterized by a high degree of suppression of axial motion artifacts. However, in order to record measuring variables in the anterior portion of the eye, such as the depth of the anterior chamber, lens thickness, etc. using the same method, there is the problem that light reflected from the particular boundary surface must be spatially superimposed on the reference reflection (usually the corneal reflection) in such a way that the interference of the partial beams is measurable. Due to the tilting of the lens of the eye which frequently occurs in humans, and thus the tilting of the visual axis with respect to the optical axis, the reflections of the various boundary surfaces generally are not situated on the same axis, and therefore cannot interfere with one another.

When the deviation of the optical axis from the measuring axis is in the range of 1° (for example, as the result of fixation problems or nystagmus), the reflections from the cornea and lens may no longer be superimposed, so that no interference measuring signal results when the "dual-beam" principle is used. The measurement is therefore very sensitive to tilting of the eye of the patient. In addition, the fixation light always appears to the patient at an infinite point, which may prove to be disadvantageous. The position of the optical axis is sought by tilting the scanning mirror in two mutually orthogonal directions until all measuring signals from the cornea and lens may be detected at the same time. This method is extremely time-consuming, and also does not provide the desired results in all patients. This method is laborious for use in everyday clinical practice.

SUMMARY OF THE INVENTION

Embodiments of the present invention implement an approach for interferometrically measuring the anterior portion of the eye which is much less sensitive to adjustment compared to the prior art, and which allows measurement of a higher proportion of eyes with visual defects. It is the aim that the approach to be developed is characterized by high reliability and sensitivity.

The device for interferometrically measuring the eye length and the anterior portion of the eye, includes an illumination source, at least one interferometric measuring system having an external reference, various optical imaging systems, and a control and evaluation unit, wherein the illumination source has high spatial coherence and low temporal coherence, an optical imaging system is situated in front of the eye in such a way that the illumination light strikes the eye as an approximately collimated beam, a first, diffraction-limited interferometric measuring system is present for measuring the eye length and a second, non-diffraction-limited interferometric measuring system is present for measuring the anterior portion of the eye, and a further beam splitter is present and configured in such a way that the light reflected from various areas of the eye is split on the two interferometric measuring systems.

The device according to the invention relates to the field of ophthalmology, and is provided for the simultaneous interferometric measurement of the eye length and the anterior portion of the eye, the measuring device being characterized by high reliability and sensitivity.

BRIEF DESCRIPTION OF THE DRAWINGS

The invention is described in greater detail below with reference to exemplary embodiments, for which the figures show the following:

FIG. 3b: depicts an interferometric measuring system according to an example embodiment of the invention corresponding to FIG. 3a, having two detectors in the "balanced detection" system.

DETAILED DESCRIPTION

A device according to an example embodiment of the invention for interferometrically measuring the eye length and the anterior portion of the eye includes an illumination source, at least one interferometric measuring system having an external reference, various optical imaging systems, and a control and evaluation unit. The illumination source has high spatial coherence and low temporal coherence. The illumination device emits light from the NIR range having a wavelength of 700-1000 nm, for example. Furthermore, an optical imaging system is situated in front of the eye in such a way that the illumination light strikes the eye as an approximately collimated beam.

In this regard, it is advantageous that the device according to the invention has at least one image sensor, which although not absolutely necessary for the function, is practical as an adjustment aid. For coupling the illumination path and the observation beam path, the device has an appropriate beam splitter.

A first, diffraction-limited interferometric measuring system is provided for measuring the eye length, while a second, non-diffraction-limited interferometric measuring system is used for measuring the anterior portion of the eye. A further beam splitter is present in the detection beam path, and is configured in such a way that the light reflected from various areas of the eye is split on the two interferometric measuring systems.

The proposed approach is based on the observation that the optical wave reflected back from an optical boundary surface in the eye involves neither purely specular (Fresnel) reflections nor purely volume scattering, but instead, a mixed form of both phenomena. The highest intensity occurs in a small range around the glancing angle.

Knowledge gained in practice has surprisingly shown that an increased intensity of the back-scattering occurs in the vicinity of the so-called glancing angle. Although in diffraction-limited detection use is made of the volume-scattered light generated, which is re-emitted uniformly in essentially all directions, at least a rough preadjustment of the optical axis of the opthalmological measuring device with respect to the visual axis would result in greatly improved measuring results.

Figure 1:
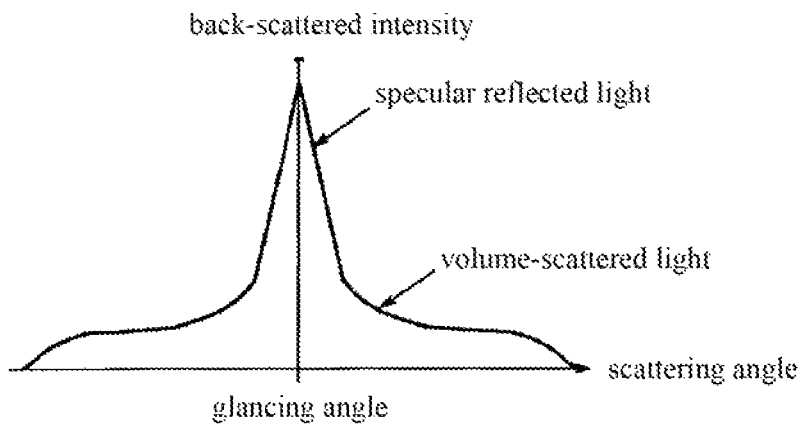
FIG. 1: depicts the intensity of the light components back-scattered from a boundary surface in the eye, as a function of the scattering angle.

In this regard, FIG. 1 depicts the intensity curve of the light components back-scattered from a boundary surface in the eye, as a function of the scattering angle. It is seen that the back-scattered light components have a much higher intensity in a narrow range around the so-called glancing angle than in the remaining range.

It is therefore advantageous to select a detection geometry which ensures, even with a certain tilting of the lens of the eye, that the signal components emitted around the glancing angle reach the detector and may be used for the interferometric measurement.

A first advantageous embodiment provides for the use of an illumination source having high spatial coherence and low temporal coherence in the form of LEDs, multimode laser diodes or superluminescent diodes. In principle, however, any type of light source having good spatial coherence and poor temporal coherence may be used as an illumination source.

A second advantageous embodiment relates to the configuration of the interferometric measuring systems. While the first, diffraction-limited interferometric measuring system for measuring the eye length may have a free beam and/or fiber optics design, the measuring arm of the second, non-diffraction-limited interferometric measuring system for measuring the anterior chamber may be designed as a free beam optical system, and its reference arm may have a free beam or fiber optics design. Mach-Zender systems and/or Michelson systems may be used as interferometric measuring systems.

The two interferometric measuring systems are connected to one another via a shared variable delay line as an external reference which is present in the reference arm of the interferometric measuring systems. Rotating or also linearly moved systems having plane mirrors, prisms, or similar optical elements are usable as a variable delay line. In addition, it is advantageous for the reference arm lengths of the two interferometric measuring systems to be coordinated with one another in such a way that the depth measuring areas do not completely overlap.

This has the further advantage that a complete depth scan over the entire eye is not necessary for this measuring system, since this depth scan results from the partial scans of the two interferometric measuring systems and a fixed quantity, which results from the known difference of the reference arm lengths and is therefore known.

In another example embodiment, the interferometric measuring systems for detecting the interference signals in each case have two detectors in the "balanced detection" system. A 50:50 beam splitter is situated in the detection beam path, in front of each of the two detectors, for splitting the interference signals.

Since the intensity of the measuring light reflected from the eye is much less than the illumination light, it is advantageous for the interferometric evaluation if the beam splitter for coupling the reference arm and the measuring arm of the diffraction-limited interferometric measuring system has an unbalanced dividing ratio. In this regard, starting from the illumination source, a dividing ratio of approximately 20:80 has proven suitable. It may thus be ensured that the measuring light essentially completely reaches the interferometric measuring system and is usable for the measurement.

However, by using a polarization beam splitter and corresponding polarizers or wave plates, it can be ensured that the illumination light as well as the measuring light pass essentially completely through the beam splitter.

In another preferred embodiment, a shutter is situated in the measuring arm of the non-diffraction-limited interferometric measuring system, in front of the beam splitter, for coupling the reference arm and the measuring arm. In this way, the light components of the measuring radiation whose path length difference is greater than $\lambda/2$ and which thus reduce the measurable interference contrast may be masked.

According to one embodiment, the beam splitter for coupling the illumination path and the detection beam path represents the most essential feature of the invention, since it splits the light reflected from various areas of the eye on the two interferometric measuring systems. To this end, the beam splitter is designed as a partially mirror-coated element, as a mirror having small dimensions, or as a selective mirror element which in its center has a reflective area and a transmissive area surrounding same. In another design, however, the beam splitter may also be designed as an aperture mirror or as a selective mirror element which in its center has a transmissive area and a reflective area surrounding same. In principle, half-mirrors or 50:50 beam splitters are also usable for this purpose, although they entail correspondingly large losses. With good signal intensities and/or highly sensitive detectors, in some circumstances these losses may be accepted.

The mode of operation of the proposed technical approach is described in greater detail below with reference to example embodiments.

Figure 2A:
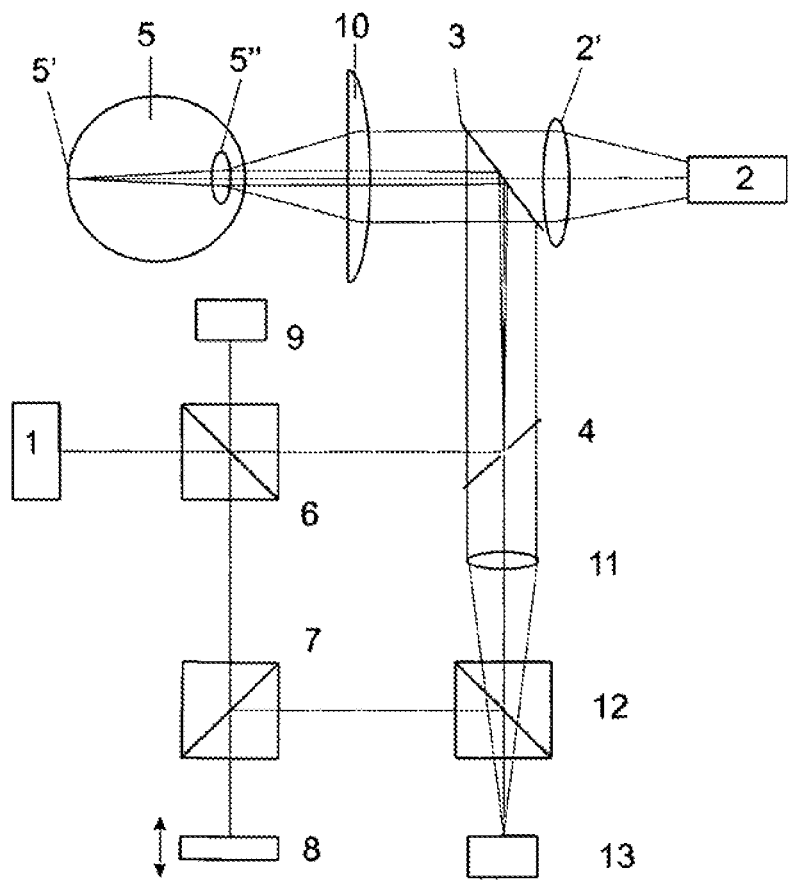
FIG. 2a: depicts an interferometric measuring system according to an example embodiment of the invention, in the free beam optical system.

To this end, FIG. 2a depicts an interferometric measuring system according to the invention, in the free beam optical system.

The device according to an example embodiment of the invention for interferometrically measuring the eye length and the anterior portion of the eye includes the illumination source 1 having high spatial coherence and low temporal coherence, a first, diffraction-limited interferometric measuring system for measuring the eye length, a second, non-diffraction-limited interferometric measuring system for measuring the anterior portion of the eye, an image sensor 2, a beam splitter 3 for coupling the illumination path and the observation beam path, and a control and evaluation unit. A further beam splitter 4 for coupling the illumination path and the detection beam path is present, and is situated in such a way that light reflected from different areas of the eye 5 is split on the two interferometric measuring systems. The image sensor 2 together with the associated imaging optics 2' is used primarily for aligning the device with the eye 5 to be measured, but may also be used for observation during the measurement.

The light from the illumination source 1 is split by the beam splitter 6 of the diffraction-limited interferometric measuring system into a measuring light component and a reference light component, the reference light component being used for both interferometric measuring systems, and being split by the beam splitter 7 on both interferometric measuring systems.

While the reference light components of the light from the illumination source 1 are imaged directly on the detectors 9 and 13 via a linear movable delay line 8 and the beam splitter 7 for coupling the two interferometric measuring systems, the measuring light component of the light from the illumination source is imaged on the eye 5 as an approximately collimated beam via the further beam splitter 4 for coupling the illumination path and the detection beam path, the beam splitter 3 for coupling the illumination path and the observation beam path, and the optical imaging system 10 situated in front of the eye 5. The diameter of the collimated beam should be in the range of 1 mm-6 mm. This radiation is focused by the eye 5 at least partially on the optical fundus 5', while the other portion is reflected on the boundary surfaces of the anterior portion of the eye 5".

The light back-scattered from the optical fundus 5' returns over the same path, and via the optical imaging system 10 and the beam splitters 3, 4, and 6 is superimposed on the reference light component of the light from the illumination source 1 and imaged on the detector 9.

The optical imaging system 10 is for example designed in such a way that the light back-scattered from the optical fundus 5' forms an intermediate focus on the beam splitter 4, so that the mirrored area may be very small, with a diameter of approximately 0.5-1 mm.

The light reflected in the anterior portion of the eye 5" is approximately collimated by the optical imaging system 10, relayed by the beam splitter 3, superimposed on the reference light component of the light from the illumination source 1, and imaged on the detector 13 via the imaging optics 11 and the beam splitter 12. According to the invention, the beam splitter 4 for coupling the illumination path and the detection beam path is designed as a mirror having small dimensions or as a selective mirror element which in its center has a reflective area and a transmissive area surrounding same. The light reflected in the anterior portion of the eye 5" travels unhindered past the mirror having small dimensions, or through the transmissive area of the selective mirror element.

Figure 2B:
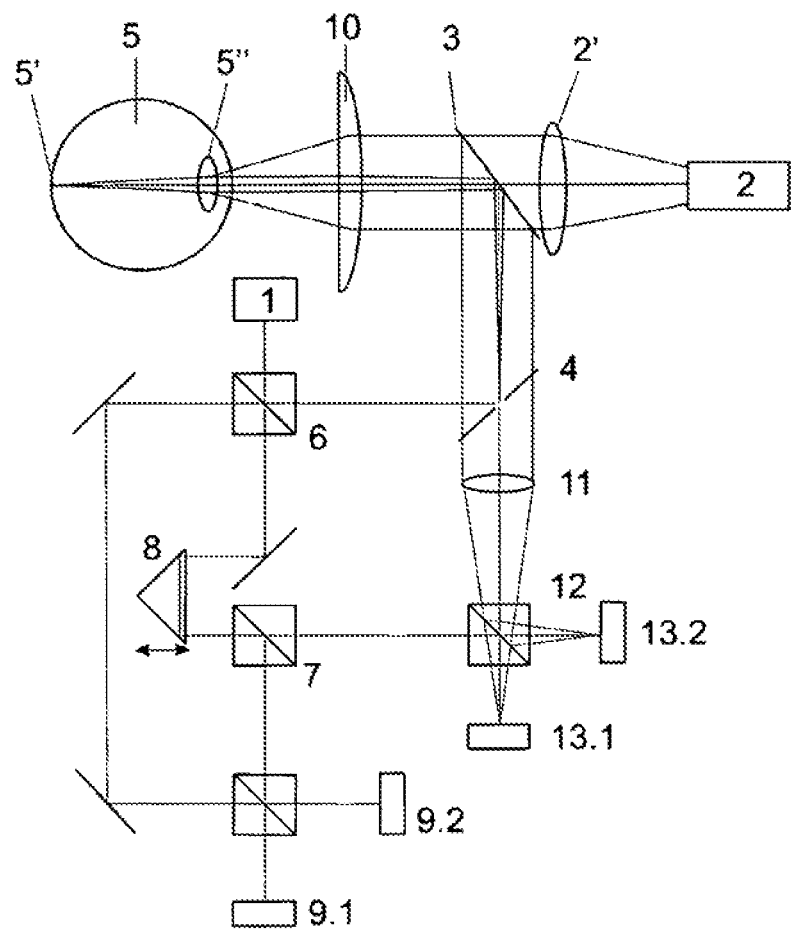
FIG. 2b: depicts an interferometric measuring system according to an example embodiment of the invention corresponding to FIG. 2a, having two detectors in the "balanced detection" system.

According to one particularly advantageous embodiment, the measured values are detected in the two interferometric measuring systems using two detectors in the "balanced detection" system. In this regard, FIG. 2b shows an interferometric measuring system according to the invention corresponding to FIG. 2a, having two corresponding detectors 9.1 and 9.2, and 13.1 and 13.2, respectively, in the "balanced detection" system. Measuring light and reference light components of a beam splitter 4 or 7 in each case are split and superimposed on the detectors 9.1 and 9.2, and 13.1 and 13.2, respectively.

According to the invention, the interferometric measurement of the anterior portion of the eye is achieved using a non-diffraction-limited interferometer whose measuring arm must necessarily be constructed in the free beam optical system, while its reference arm may be designed in the free beam optical system or the fiber optics system. By using a non-diffraction-limited free beam optical system in the measuring arm, it may be ensured, as required, that the light reflected back from the anterior boundary surfaces of the eye at the glancing angle may be detected by the detector and recorded, even if the axis of the eye is tilted with respect to the system axis of the optical imaging system.

In contrast, the eye length is measured using a diffraction-limited interferometric measuring system, which may be designed completely in the free beam optical system and/or fiber optics system.

Figure 3A:
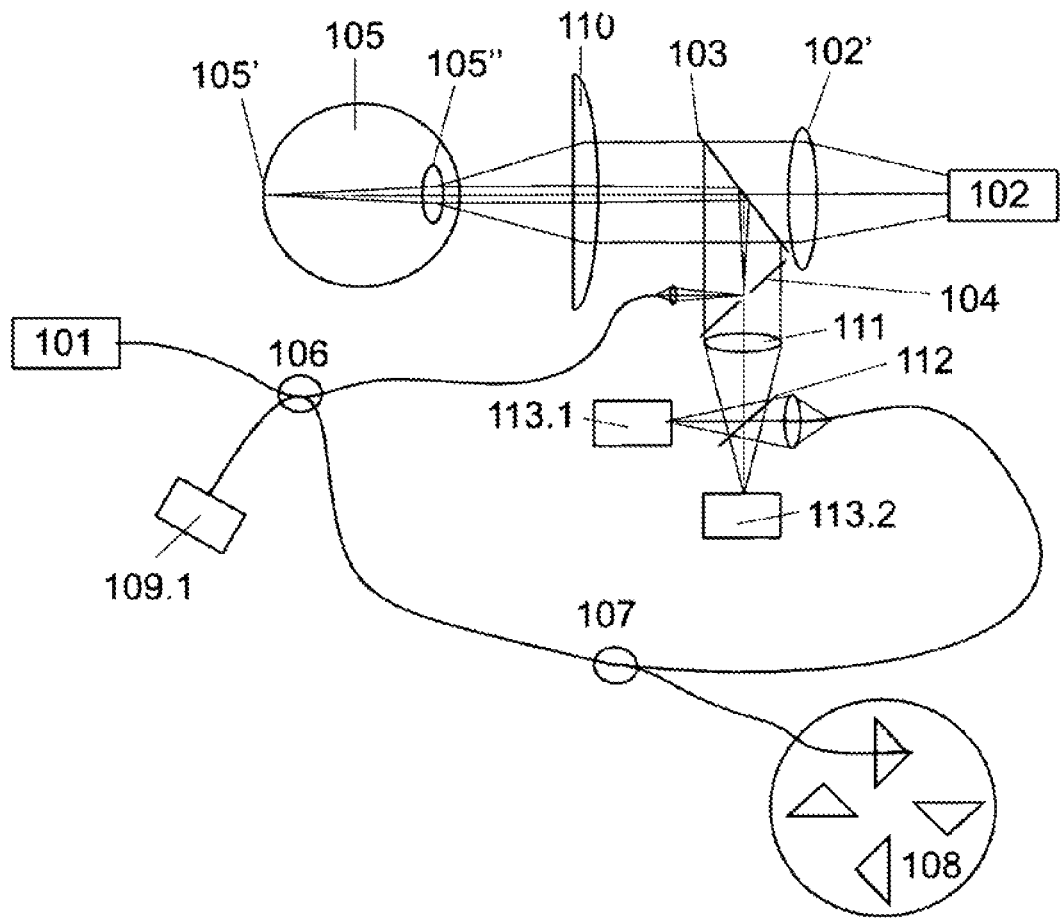
FIG. 3a: depicts an interferometric measuring system according to an example embodiment of the invention in a combined free beam optical system/fiber optics system.

FIG. 3a depicts an interferometric measuring system according to and embodiment of the invention in a combined free beam/fiber optics design, and FIG. 3b shows the two corresponding detectors in the "balanced detection" system for both interferometers.

In this regard, the optical paths in the two interferometric measuring systems have been designed as fiber optics where possible. To this end, preferably single-mode fibers having corresponding optical elements are used for coupling and decoupling the light radiation. The device according to the invention for interferometrically measuring the eye length and the anterior portion of the eye corresponds to that described for FIGS. 2a and 2b. Here as well, the image sensor 102 together with the associated imaging optics 102' are used primarily for aligning the first device with the eye 105 to be measured, but may also be used for observation during the measurement.

The light from the illumination source 101 is coupled into a single-mode fiber, and is split by the fiber coupler 106 of the diffraction-limited interferometric measuring system into a measuring light component and a reference light component, the reference light component being used for both interferometric measuring systems, and split on both interferometric measuring systems by the fiber coupler 107.

While the reference light component of the light from the illumination source 101 is imaged directly on the detectors 109 and 113 via a rotating delay line 108 and the fiber coupler 107 for coupling the two interferometric measuring systems, the measuring light component of the light from the illumination source is imaged on the eye 105 as an approximately collimated beam via the beam splitter 104 for coupling the illumination path and the detection beam path, the beam splitter 103 for coupling the illumination path and the observation beam path, and the optical imaging system 110 situated in front of the eye 105. Here as well, the diameter of the collimated beam should be in the range of 1 mm-6 mm. The radiation is focused by the eye 105 at least partially on the optical fundus 105', while the other portion is reflected on the boundary surfaces of the anterior portion of the eye 105".

The light back-scattered from the optical fundus 105' returns over the same path, and via the optical imaging system 110 and the beam splitters 103, 104 and the fiber coupler 106 is superimposed on the reference light component of the light from the illumination source 101 and imaged on the detector 109 via the fiber coupler 114.

The light reflected in the anterior portion of the eye 105" is approximately collimated by the optical imaging system 110, relayed by the beam splitter 103, superimposed on the reference light component of the light from the illumination source 101, and imaged on the detectors 113.1 and 113.2 via the imaging optics 111 and the beam splitter 112, it also being possible to dispense with one of the two detectors 113.1 or 113.2. According to the invention, the beam splitter 104 for coupling the illumination path and the detection beam path is designed as a mirror having small dimensions or as a selective mirror element which in its center has a reflective area and a transmissive area surrounding same. The light reflected in the anterior portion of the eye 105" travels unhindered past the mirror having small dimensions, or through the transmissive area of the selective mirror element.

According to another example embodiment, here as well the measured values are detected in both interferometric measuring systems using two detectors in the "balanced detection" system. In this regard, FIG. 3b shows an interferometric measuring system according to the invention corresponding to FIG. 3a, having two corresponding detectors 109.1 and 109.2, and 113.1 and 113.2, respectively, in the "balanced detection" system. In this regard, measuring light and reference light components are split by beam splitters 114 and 112 and superimposed on the two detectors 109.1 and 109.2 and 113.1 and 113.2, respectively.

In this regard it should be noted that the detectors used in the two interferometric measuring systems have distinct differences.

In contrast to the detectors for diffraction-limited detection, on account of the large-surface detection the detectors used in the non-diffraction-limited interferometric measuring system must have an active detector surface which is much larger than the resolution limit of the optical imaging system.

A final advantageous embodiment provides for the use of an optical imaging system having a large aperture, since the largest possible quantity should be "collected" from the light reflected from the anterior portion of the eye.

The device according to the invention provides an approach for interferometrically measuring the eye length and the anterior portion of the eye which is characterized by high reliability and sensitivity. The proposed approach allows simultaneous measurement of the eye length and the anterior portion of the eye, which has the advantage that the measurements may be made either more rapidly or with greater care, since more time is available for the measurement.

Compared to the prior art, the proposed approach is much less sensitive to adjustment, and allows measurement of a higher proportion of eyes with visual defects.

By using a non-diffraction-limited free beam optical system in the measuring arm, it may be ensured, as required, that the light reflected back from the anterior boundary surfaces of the eye at the glancing angle may be detected by the detector and recorded, even if the axis of the eye is tilted with respect to the system axis of the optical imaging system.

Thus, the proposed device differs from the known approaches of the prior art, which detect either diffraction-limited scattered light signals or reflected signals at the glancing angle, but which require that the optical axis of the eye to be measured be aligned beforehand with the system axis of the detection optics, with cooperation by the patient.

The invention claimed is:

1. A device for interferometrically measuring the eye length and the anterior portion of the eye, comprising:
    an illumination source producing illumination light;
    two interferometric measuring systems, at least one of the two interferometric measuring systems comprising a delay line as an external reference;
    various optical imaging systems; and
    a control and evaluation unit;
    wherein the illumination source has high spatial coherence and low temporal coherence and an optical imaging system is situated in front of the eye such that the illumination light strikes the eye as an approximately collimated beam,
    wherein the two interferometric measuring systems comprise a first, diffraction-limited interferometric measuring system that measures the eye length and a second, non-diffraction-limited interferometric measuring system that measures the anterior portion of the eye, and a beam splitter that couples an illumination path and a detection beam and which is configured such that light reflected from various areas of the eye is split into the two interferometric measuring systems.

2. The device according to claim 1, wherein the illumination source comprises LEDs, multimode laser diodes or superluminescent diodes.

3. The device according to claim 1, wherein the illumination source comprises multimode laser diodes.

4. The device according to claim 1, further comprising at least one image sensor.

5. The device according to claim 1, wherein the first, diffraction-limited interferometric measuring system for measuring the eye length comprises a free beam and/or fiber optics design.

6. The device according to claim 1, wherein the second non-diffraction limited interferometric measuring system comprises a measuring arm and a reference arm and wherein the measuring arm of the second, non-diffraction-limited interferometric measuring system for measuring the anterior chamber of the eye comprises a free beam optical system, and the reference arm of the second, non-diffraction-limited interferometric measuring system comprises a free beam or fiber optics design.

7. The device according to claim 1, wherein the first, diffraction-limited interferometric measuring system or the second, non-diffraction-limited interferometric measuring system comprise Mach-Zender systems, Michelson systems or a combination thereof.

8. The device according to claim 1, wherein both the first diffraction limited interferometric measuring system and the second non-diffraction limited interferometric measuring system each comprise a measuring arm and a reference arm and wherein the first, diffraction-limited interferometric measuring system and the second, non-diffraction-limited interferometric measuring system are connected to one another via a shared variable delay line as an external reference which is present in the reference arm of the first, diffraction-limited interferometric measuring system or the second, non-diffraction-limited interferometric measuring system.

9. The device according to claim 8, wherein the variable delay line comprises rotating or linearly moved systems.

10. The device according to claim 1, wherein both the first diffraction limited interferometric measuring system and the second non-diffraction limited interferometric measuring system each comprise a measuring arm and a reference arm and wherein reference arm lengths of the first, diffraction-limited interferometric measuring system and the second, non-diffraction-limited interferometric measuring system are coordinated with one another in such a way that depth measuring areas of the first, diffraction-limited interferometric measuring system and the second, non-diffraction-limited interferometric measuring system do not completely overlap.

11. The device according to claim 1, wherein the first, diffraction-limited interferometric measuring system and the second, non-diffraction-limited interferometric measuring system each have two detectors which are configured in a "balanced detection" system having a 50/50 beam splitter in a detection beam path that splits interference signals between the two detectors.

12. The device according to claim 1, wherein both the first diffraction limited interferometric measuring system and the second non-diffraction limited interferometric measuring system each comprise a measuring arm and a reference arm and wherein the first, diffraction-limited interferometric measuring system further comprises a further beam splitter for coupling the reference arm and the measuring arm of the first, diffraction-limited interferometric measuring system and the further beam splitter has an unbalanced dividing ratio.

13. The device according to claim 12, wherein the unbalanced dividing ratio is approximately 20:80, based on the illumination source.

14. The device according to claim 1, wherein both the first diffraction limited interferometric measuring system and the second non-diffraction limited interferometric measuring system each comprise a measuring arm and a reference arm and wherein the measuring arm of the second, non-diffraction-limited interferometric measuring system further comprises a shutter in front of a further beam splitter, for coupling the reference arm and the measuring arm.

15. The device according to claim 1, wherein the beam splitter that couples the illumination path and the detection beam path is designed as a partially mirror-coated element.

16. The device according to claim 1, wherein the beam splitter that couples the illumination path and the detection beam path comprises as a selective mirror element which, in a center thereof, has a reflective area and a transmissive area surrounding the reflective area.

17. The device according to claim 1, wherein the beam splitter that couples the illumination path and the detection beam path comprises a mirror.

* * * * *

UNITED STATES PATENT AND TRADEMARK OFFICE
CERTIFICATE OF CORRECTION

| | | |
|---|---|---|
| PATENT NO. | : 9,161,687 B2 | Page 1 of 1 |
| APPLICATION NO. | : 13/995351 | |
| DATED | : October 20, 2015 | |
| INVENTOR(S) | : Tobias Schmitt-Manderbach et al. | |

It is certified that error appears in the above-identified patent and that said Letters Patent is hereby corrected as shown below:

In the specification
Col. 7, line 45, delete "and" and insert --an--

Signed and Sealed this
Ninth Day of August, 2016

Michelle K. Lee
*Director of the United States Patent and Trademark Office*